United States Patent [19]
Cheong

[11] Patent Number: 5,352,508
[45] Date of Patent: Oct. 4, 1994

[54] NET WOUND DRESSINGS

[75] Inventor: Catherine L. Cheong, Burnley, United Kingdom

[73] Assignee: Johnson & Johnson Medical, Inc., Arlington, Tex.

[21] Appl. No.: 28,924

[22] Filed: Mar. 4, 1993

Related U.S. Application Data

[63] Continuation of Ser. No. 828,263, Jan. 30, 1992, abandoned.

[30] Foreign Application Priority Data

Jan. 31, 1991 [GB] United Kingdom ............ 9102089.1

[51] Int. Cl.$^5$ ................................................ B32B 7/00
[52] U.S. Cl. .................................... 428/264; 428/267; 428/270; 428/290; 428/332; 427/211; 427/248; 427/359; 424/443
[58] Field of Search .................. 424/443, 444, 445; 523/111

[56] References Cited

U.S. PATENT DOCUMENTS

| | | | |
|---|---|---|---|
| 4,404,296 | 9/1983 | Schäpel | 523/105 |
| 4,524,064 | 6/1985 | Nambu | 424/81 |
| 4,661,099 | 4/1987 | von Bittera | 604/290 |
| 4,904,247 | 2/1990 | Therriault | 604/304 |
| 4,929,577 | 5/1990 | Cornell | 514/58 |
| 4,960,594 | 10/1990 | Honeycutt | 424/445 |
| 5,035,893 | 6/1991 | Shioya | 424/447 |
| 5,156,601 | 10/1992 | Lorenz | 424/445 |

FOREIGN PATENT DOCUMENTS

| | | |
|---|---|---|
| 0059048 | 9/1982 | European Pat. Off. |
| 1153332 | 3/1958 | France . |
| 74684/91 | 9/1991 | PCT Int'l Appl. ......... A61F 13/00 |
| 8705206 | 9/1987 | World Int. Prop. O. . |
| 8801878 | 3/1988 | World Int. Prop. O. . |

Primary Examiner—Gabrielle Phelan

[57] ABSTRACT

A net dressing in which the net substrate is encapsulated in a hydrophilic, tacky resin, the coating on the net substrate leaving the majority of the apertures in the net substrate unoccluded and a process for preparing the dressing.

11 Claims, No Drawings

NET WOUND DRESSINGS

This is a continuation of application Ser. No. 828,263, filed Jan. 30, 1992, now abandoned.

The present invention relates to a net wound dressing in particular, but not exclusively, for use in treating exuding wounds such as burns and ulcers.

Many types of wound dressings are known in the art. These range from small sticking plasters, used to cover minor cuts and abrasions, to large dressings used during surgery or in the treatment of large wounds. Dressings known in the prior art are made from a wide variety of materials. Most dressings comprise a support layer, such as a plastics film, which may be occlusive or micro- or macro-porous, a foamed plastic or a knitted, woven or non-woven fabric, which may be made from natural and/or synthetic fibres.

Generally, the substrate is coated on one of its faces with an adhesive. The most commonly used adhesives are based on natural or synthetic rubbers or on acrylic polymers. Rubber-based adhesives are disadvantageous in that they adhere strongly to skin and when a dressing using such an adhesive is removed, some at least of the adhesive remains on the skin.

A disadvantage of acrylate-based adhesives is that they are generally water-impermeable and occasionally cause skin irritation. Their use can therefore lead to damage to healthy skin surrounding a wound which is being treated.

A further disadvantage of both rubber- and acrylate-based adhesives is that they generally adhere very strongly to themselves. Thus, if a dressing is mishandled and one area of the adhesive layer contacts another area, it is difficult to separate the contacting areas. They may also adhere to wound areas and, if allowed to contact wound areas, might interfere with the wound healing process.

In most dressings used to treat wounds, an absorbent pad is placed over part of the area covered by the adhesive in order to absorb any exudate from the wound. This also prevents the adhesive from coming into contact with the wound.

Improved dressings of this type are described in U.S. Pat. No. 4,661,099 (von Bittera et al.). The improvements in the dressings relate to the adhesive used. This is a polyurethane adhesive containing within its matrix a polymeric polyol. U.S. Pat. No. 4,661,099 describes conventional dressings for treating non- or lightly-exuding wounds. These dressings have an absorbent pad covering the adhesive layer. U.S. Pat. No. 4,661,099 also describes elastic or inelastic fabrics coated with the adhesive. These adhesive-coated fabrics are intended for use in affixing conventional dressings to a wound or as surgical tapes.

Another sort of dressing known in the art is a net dressing. The substrate used in a net dressing is an apertured material made from natural or synthetic fibres. The material may be woven, knitted or non-woven and has a regular pattern of apertures, generally having a diameter or width of 0.5 to 5 mm. Net dressings are generally used on wounds which are exuding large amounts of fluid, in particular to act as a non-adherent layer placed between the wound and an absorbent layer, to prevent the absorbent layer sticking to the wound.

One known type of net dressing which is commercially available comprises a net substrate which has been coated with a paraffinic material. Another known type of net dressing which is commercially available comprises a net substrate coated with a mixture of povidone-iodine (a complex of iodine and polyvinylpyrrolidone) and polyethylene glycols.

Most of these commercially available net dressings are hydrophobic. In theory, they therefore do not stick to exuding wounds and allow the exudate to pass through them. They have therefore been used successfully for emergency treatment of exuding wounds. However, they cannot be used for long periods and have other disadvantages. The main disadvantage is that the paraffinic material of these net dressings is easily removed from the net substrate, for instance during handling when the dressing is applied or repositioned. This tends to leave the net substrate exposed to the wound. The coating on the dressing is also removed from the net substrate in the course of time, during use, again leaving the substrate exposed to the wound.

This removal of the coating leads to the substrate coming into contact with the exudate and the healing wound. Such contact can interfere, in some cases substantially, with the wound healing process and can allow the substrate to stick to the wound and thus can cause damage on removal.

Another disadvantage is that the net dressings are greasy and are thus difficult to apply.

IWO-A-8 705 206 (Fabo) proposes an improved net dressing. The proposed dressing comprises an elastic net substrate which has been encapsulated in a hydrophobic gel, leaving open the apertures in the net substrate. The only hydrophobic gel mentioned in WO-A-8 705 206 is a silicone gel marketed by Dow Corning under the trade name Q7-2218. However, the only example given of a net dressing using this gel does not provide any disclosure of the properties such a net dressing would have. It is merely indicated in WO-A-8 705 206 that a silicone gel-coated net dressing may be flexible, self-adhering and reshapeable.

It is indicated in WO-A-8 705 206 that the silicone gel could be replaced by a polyurethane gel. However, there is no guidance given as to which sort of polyurethane gel should be used, nor of the properties, other than hydrophobicity, the polyurethane gel should have.

The silicone-coated net dressings proposed in WO-A-8 705 206 have a number of disadvantages. Firstly, the silicone gel is a relatively expensive material and so silicone-coated net dressings will also be relatively expensive. The adhesive will also not tack well to wet skin, thus making it difficult to locate the dressing on a wound. Moreover, the hydrophobic nature of the gel will tend to prevent extraction of any medicaments incorporated in the gel, thus reducing or eliminating their effectiveness.

It is an object of the present invention to provide an improved net dressing.

Accordingly, the present invention provides a net dressing in which the net substrate is encapsulated in a hydrophilic, tacky resin, the coating on the net substrate leaving the majority of the apertures in the net substrate unoccluded.

Preferably, the hydrophilic, tacky resin comprises a high molecular weight crosslinked polyurethane matrix containing at least one polyhydroxy compound having a number average molecular weight from 1,000 to 12,000 and a number average hydroxyl value from 26 to 110, the polyhydroxy compound(s) comprising from 40 to 85% by weight (based on the total weight of the matrix and the polyhydroxy compound(s)), the resin being essentially free of polyhydroxy compounds having a molecular weight below 800.

Alternatively, the hydrophilic, tacky resin comprises a polymerised hydrogel, such as a derivatised polyacrylamide copolymer containing sulphonate groups. Particularly suitable resins are Promeon Hydrogel RG60 series resins, for example the RG63B resin. This is the sodium salt of a UV-polymerised acrylamidopropane sulphonic acid. Promeon Hydrogels are supplied by Promeon, a division of Medtronic, Inc., of Minneapolis, Minn., USA.

Preferably, at least 75% and most preferably at least 90% of the apertures in the net substrate are unoccluded. Advantageously, substantially all of the apertures are unoccluded.

Preferably, the matrix contains from 45 to 80%, most preferably from 55 to 75%, of the at least one polyhydroxy compound. Advantageously, the polyhydroxy compound(s) has a number average molecular weight from 1,500 to 8,000, most preferably from 2,000 to 6,000. Conveniently, the resin is essentially free of polyhydroxycompounds having a molecular weight below 1,000, more preferably 1,500.

The resin may contain conventional fillers or additives. The total weight of fillers and additives used preferably should not exceed the total weight of the matrix and the polyhydroxy compound(s). A particularly useful, but not essential, additive is a medication, for example: chlorhexidine or one of its derivatives, such as chlorhexidine hydrochloride, acetate or gluconate; povidone-iodine; a quaternary ammonium salt such as cetyl pyridinium chloride; silver sulphur diazine; a local anaesthetic; or a growth factor.

Where the resin is a polyurethane resin, it will, of necessity, contain the residue of the catalyst used to produce the crosslinked polyurethane matrix.

The polyurethane resin which is preferred for use in the present product may be obtained by reacting a polyisocyanate with an excess of the at least one polyhydroxy compound as defined above. The polyisocyanate will have a minimum isocyanate functionality of 2 and preferably will have an isocyanate functionality of no more than 4. The polyisocyanate may be aliphatic, cycloaliphatic or aromatic. Suitable polyisocyanates include 1,6-hexamethylene diisocyanate, 4,4'-dicyclohexylmethane diisocyanate, 4,4'-diphenylmethane diisocyanate, 2,4-toluylenic diisocyanate and biurets, trimers, isomers or mixtures thereof. A particularly preferred polyisocyanate is Desmodur ®N, supplied by Bayer AG, which is 1,6-hexamethylene diisocyanate which has been biuretised. It has an average isocyanate functionality of 3.6 and a number average molecular weight of 700.

The polyhydroxy compound is preferably prepared by the addition of ethylene oxide and/or propylene oxide to a suitable polyfunctional base molecule. Suitable base molecules include pentaerythritol, sorbitol, trimethylolpropane and ethylenediamine. Preferred polyhydroxy compounds have from 0 to 55% of added ethylene oxide groups and from 100 to 45% of added propylene oxide groups. A particularly preferred polyhydroxy compound is Levagel ®, supplied by Bayer AG.

Any conventional catalyst may be used to initiate the reaction between the polyisocyanate and the polyhydroxy compound(s). Suitable catalysts include tertiary amines, Mannich bases, sila-amines containing carbon-silicon bonds and organometallic compounds, especially organotin compounds. Preferred catalysts are organotin compounds such as the tin salts of organic acids and dialkyl tin salts of organic acids. A particularly preferred catalyst is dibutyl tin dilaurate.

In general, the resin will be formed by reacting together from 4 to 8 parts of the polyisocyanate, from 0.01 to 0.06 parts of catalyst and 100 parts of polyhydroxy compound(s), optionally in the presence of up to 100 parts in total of fillers and/or additives.

The resin may be produced merely by adding all the components into a mixer and mixing thoroughly to initiate polymerisation. Alternatively, the resin may be produced by forming a prepolymer. The prepolymer may be formed by reacting all the polyisocyanate with a fraction of the polyhydroxy compound(s). Alternatively, the prepolymer may be formed by reacting all the polyhydroxy compound(s) with a fraction of the polyisocyanate. Thereafter, the prepolymer is mixed with the remaining components to complete the formation of the resin.

Polyurethane resins suitable for use in the present invention are described in general terms in U.S. Pat. No. 4,404,296 (Schäpel). The resins described in U.S. Pat. No. 4,404,296 have very varied properties and many of them would be unsuitable for use in the present invention. In order to obtain a resin of the appropriate properties for use in the present invention, it is necessary to observe the limitations referred to above.

It will be appreciated that the relative amounts of reactants, the total mass of reaction mixture, the mixing time, the method of mixing and the temperature of the reaction will need to be selected so as to produce a reasonable gel time. If the gel time is too short, it may be impossible to coat the resin onto the substrate, or the resin may occlude substantially all of the apertures in the net. If the gel time is too long, the resin may not completely encapsulate the net substrate and may form into drops on the substrate.

The net substrate used to produce the net dressing of the present invention may be any one of those net substrates already known for use in net dressings. However, it is preferred that the net substrate is made from inelastic fibers. It is further preferred that the net substrate is made from continuous fibers.

The use of inelastic fibers is advantageous in that it ensures that not too much pressure is applied to the wound. It is also difficult to manufacture the dressing using elastic fibres. The use of continuous fibers is advantageous because it assists in ensuring that the wound healing process is not interfered with. If staple length fibers are used, it has been observed that fibers may work loose from the substrate and penetrate the coating resin. These protruding fibers can then contact the wound and interfere with the wound healing process. Moreover, the protruding fibers tend to reduce the tack of the polyurethane resin in areas away from the wound.

The protruding fibers also tend to prevent the curing of the gel and will prevent the formation of a continuous coating. If a continuous coating is not present, then parts of the gel may break off and fall into the wound.

The substrate may be knitted, woven or non-woven. Preferably, the substrate has a basis weight from 25 to 200 g.m$^{-2}$, most preferably 50 to 100 g.m$^{-2}$. The smallest dimension of each aperture is preferably from 0.5 to 5.0 mm, most preferably from 1.0 to 3.0 mm.

The fibres may be cotton, wool, rayon, polyamide, polyimide, polypropylene or polyester fibers or mixtures thereof. A preferred fibre is a knitted polyester fabric made by Brightwake Limited of Kirkby-in-Ashfield, Notts., U.K. under the designation 2632. This has a basis weight of about 85 g.m$^{-2}$ and a thread count of 120 wales per 10 cm and 138 courses per 10 cm.

The amount of resin coated onto the net substrates is preferably from 25 to 300 g.m$^{-2}$, most preferably from 50 to 150 g.m$^{-2}$. It should, of course, be ensured that sufficient resin is used to encapsulate all the substrate without occluding the apertures.

The net dressing of the present invention is preferably produced in a continuous process wherein a web of the net substrate is passed through the nip of a pair of coating rollers, wherein the polyurethane resin is applied to the substrate. If desired, on emerging from the nip, the coated substrate may be subjected to a blast of air to reopen any apertures which may have been occluded during the coating.

The resin may be applied to the coating rollers from a bath in which one of the rollers is partially immersed. In this case, the resin will need to be slow-curing so that it does not cure in the bath. In order to accelerate curing once the resin has been coated onto the substrate, the coated substrate may be passed through one or more heating zones.

Alternatively, the resin may be applied from a feeder directly to the nip of the rollers. In this case, the resin may be prepared on a continuous basis and can therefore be of a much more quick-curing nature. In this case, there may be no need for any heating zones.

In either case, it may be advisable, depending on the resin used, to cool the rollers to prevent the resin curing thereon. Alternatively, it may be advisable to locate scrapers adjacent the rollers so that any resin which cures on the rollers is scraped off before the resin feeding point.

By controlling the curing time, it is also possible to obtain a dressing which is more tacky on one side than on the other. If the resin is relatively slow curing, during the cure stage the resin will "drop" so that there is more resin on one side of the substrate than the other. The side with the thicker coating will be more tacky than the other side. This can be advantageous where it is desired to locate an absorbent pad on the side of the dressing remote from the wound. The absorbent layer can be located securely on the more tacky side, while the less tacky face is placed over the wound. This minimises the possibility of the dressing adhering too strongly to the wound or the area around it.

The coated substrate may be laminated between two layers of release sheet. These may comprise sheets of plastic which inherently have low tack for the resin used or which have been treated so as to have the required low tack. Alternatively, the release sheets may be sheets of paper which have been treated to reduce their tack to the resin used.

The net dressings of the present invention can be used in place of net dressings which are at present commercially available. However, they can also be used as wound closures, for instance in place of staples or stitches, or as specialist dressings for finger injuries, for use in treating burns or ulcers, or for use in plastic surgery.

The net dressings of the present invention may be used in one or more layers. If a multilayer structure is used, preferably adjacent layers are arranged at an angle of approximately 45° to each other. This allows the formation of smaller holes without substantially reducing the conformability of the dressing.

The dressings may be used in combination with absorbent pads and the pads or the dressings may be medicated.

The dressings of the present invention have a number of significant advantages. They are very conformable because the net substrate is pliant and because the coated resin does not significantly reduce this pliancy. They can therefore be easily applied to any area of the body, in particular areas such as fingers, elbows and knees which are irregular in shape and are often moved.

The present dressings are washable and can therefore be removed from a wound, cleaned and then replaced. They can also be cleaned in situ as long as care is taken to ensure that the dressing remains properly located on the wound.

The present net dressings are not greasy, whereas the commercially available prior art net dressings are. They are therefore easier to handle. Moreover, unlike the greasy coatings on the commercial net dressings, the resins used in the present invention do not become detached from the substrate. Therefore, the substrate does not come into contact with the wound and cannot interfere with the wound healing process.

The resin used in the net dressing of the present invention adheres well to dry skin but does not adhere to wet skin or to exuding wounds. It is therefore not necessary to cover the resin in the area of the wound. Despite the fact that the resin does not adhere to exuding wounds, the hydrophilic nature of the resin allows exudate to pass through the net dressing. The exudate can then be removed without disturbing the wound.

For instance, the exudate may be absorbed in an absorbent pad attached to the side of the dressing remote from the wound. This leads to another advantage of the net dressing of the present invention. Using this dressing, it is possible to replace absorbent pads placed adjacent exuding wounds, but separated therefrom by the net dressing, as soon as their capacity is reached, without needing to disturb the dressing.

A further advantage of the dressings of the present invention is that they are transparent. Thus, a physician or nurse can view the wound without needing to remove the dressing.

The resin used in the net dressings of the present invention as well as having good tack to dry skin also has good tack to itself. It is thus very easy to secure in position, even on parts such as fingers and toes. Moreover, the resin loses its tack on treatment with water. Thus, the net dressings of the present invention can readily be removed or repositioned. A further advantage is that if the dressing is lapped over on itself, although it tacks to itself, it also releases from itself readily, without removing the coating. This again contributes to the ease with which it can be secured on the wound or then removed from the wound.

The advantageous properties of the net dressing of the present invention are only obtained if a resin, as defined above, is used to encapsulate the net substrate. If other resins, such as hydrophobic polyurethane resins, are used the advantageous properties are not all obtained.

The present invention is now illustrated, by way of example only, with reference to the following description of specific, non-limiting illustrations of the preparation and use of net dressings according to the present invention.

EXAMPLE 1

A net dressing was made using as the substrate a 10 cm × 10 cm square of the Brightwake 2632 fabric referred to above. The net had square apertures which were 2 mm long on each side. The net substrate had a basis weight of 75 g.m$^{-2}$.

A resin mixture was prepared by mixing together 3.1 g of Desmodur ®N, 50 g of Levagel ® and 0.02% (by weight based on the total weight of the Levagel ®) of dibutyl tin dilaurate. Mixing was carried out for 180 seconds. The mixture was then padded onto the substrate. The coated substrate was then treated with a blast of air to open up any occluded apertures in the net. The coated substrate was then allowed to cure in air at 20° C. Cure was complete after 18 minutes from the beginning of mixing.

The net dressing thus produced had good tack to itself, but could easily be freed from itself. It had good tack to dry skin but did not tack to wet skin or to exuding wounds. The dressing was highly conformable and easy to locate on such areas as fingers and elbows. It could readily be removed by application of water. The dressing was transparent and therefore allowed ready inspection of the area to which it was adhered.

EXAMPLE 2

A second net dressing was produced using the same net substrate following the procedure set forth in Example 1, expect that the resin mixture comprised 0.04% catalyst and the mixing time was 120 seconds. The curing time in this case was 12 minutes. The second dressing had properties similar to those of the first dressing.

EXAMPLE 3

The procedure described in Example 1 was repeated except that the reaction mixture comprised 3.6 g of Desmodur, 48 g of Levagel and 0.04% catalyst. The mixing time was 90 seconds and the curing time was 10 minutes. The dressing thus produced had comparable properties to the dressing of Example 1.

EXAMPLE 4

The procedure described in Example 1 was repeated except that the reaction mixture comprised 2.9 g of Desmodur, 48 g of Levagel and 0.04% catalyst. The mixing time was 90 seconds and the curing time was 27 minutes. The dressing thus produced had comparable properties to the dressings of Example 1.

EXAMPLE 5

A continuous web of the knitted polyester net fabric described in Example 1 was fed to the nip of a pair of coating rollers. To the nip was also fed a reaction mixture comprising 3.1 parts of Desmodur, 50 parts of Levagel and 0.06% dibutyl tin dilaurate. The reaction mixture was supplied from a continuous mixer, and its residence time therein was 90 seconds. At 20° C., this mixture cured in 7 minutes.

On emerging from the nip, the coated substrate passed through an air stream which opened up any apertures which had become occluded during the coating stage. The coated net substrate was then passed through a heating zone at a temperature of 50° C. to cure the resin. The coated substrate was then sandwiched between two sheets of siliconised release paper. The dressing thus produced had comparable properties to the dressing of Example 1.

EXAMPLE 6

Example 5 was repeated, except that instead of using the continuous mixer, the resin was supplied to the nip of the rollers from a bath in which the cover roller was partially immersed. The bath contained a reaction mixture comprising 3.1 parts of Desmodur, 50 parts of Levagel and 0.02% catalyst. The mixture was mixed for 60 seconds prior to placing it in the bath. This reaction mixture cured at 20° C. in 30 minutes. In this case, the heating zone was maintained at 80° C. and this allowed the resin to be cured in 2 minutes.

The dressings thus produced had comparable properties to the dressings of Example 1.

It will be appreciated that the present invention has been described above by way of example only and that variations and modifications may be made, as will be apparent to the skilled man, without departing from the scope of the invention.

I claim:

1. A pliant and comformable net dressing that adheres well to dry skin but does not adhere to wet skin and that comprises a net substrate, which has apertures whose smallest dimension is about 1.0 to 3.0 mm and which is encapsulated in a hydrophilic tacky resin, comprising either
   a polymerised hydrogel or
   a high molecular weight crosslinked polyurethane matrix containing at least one polyhydroxy compound having a number average molecular weight from 1,000 to 12,000 and a number average hydroxyl value from 26 to 110, the polyhydroxy compound comprising from 40 to 85% by weight based on the total weight of the matrix and the polyhydroxy compound, the resin being essentially free of polyhydroxy compounds having a molecular weight below 800, and
   the resin on the net substrate leaving the majority of the apertures in the net substrate unoccluded.

2. The net dressing of claim 1, wherein the hydrophilic, tacky resin comprises a high molecular weight crosslinked polyurethane matrix containing at least one polyhydroxy compound having a number average molecular weight from 1,000 to 12,000 and a number average hydroxyl value from 26 to 110, the polyhydroxy compound comprising from 40 to 85% by weight based on the total weight of the matrix and the polyhydroxy compound, the resin being essentially free of polyhydroxy compounds having a molecular weight below 800.

3. The net dressing of claim 1, wherein the hydrophilic, tacky resin comprises a polymerised hydrogel.

4. The net dressing of claim 1, wherein at least 75% of the apertures in the net substrate are unoccluded.

5. The net dressing of claim 1, wherein the resin contains fillers or additives.

6. The net dressing of claim 1, wherein the net substrate used to produce the net dressing is made from inelastic fibers.

7. The net dressing of claim 1, wherein the net substrate is made from continuous fibers.

8. The net dressing of claim 1, wherein the net substrate is knitted, woven or non-woven.

9. A continuous process for the production of the net dressing of claim 1, wherein a web of the net substrate is passed through the nip of a pair of coating rollers, wherein the resin is applied to the substrate, and on emerging from the nip, the coated substrate is subjected to a blast of air to reopen any apertures which may have been occluded during the coating.

10. The net dressing of claim 3 wherein the polymerized hydrogel is a derivatized polyacrylamide copolymer containing sulphonate groups.

11. The net dressing of claim 4 wherein at least 90% of the apertures in the net substrate are unoccluded.

* * * * *